(12) United States Patent
Lai

(10) Patent No.: US 9,028,121 B2
(45) Date of Patent: May 12, 2015

(54) ELECTRONIC CENSER

(71) Applicant: Hon Hai Precision Industry Co., Ltd., New Taipei (TW)

(72) Inventor: Chih-Chen Lai, New Taipei (TW)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 86 days.

(21) Appl. No.: 13/753,522

(22) Filed: Jan. 30, 2013

(65) Prior Publication Data

US 2014/0168945 A1    Jun. 19, 2014

(30) Foreign Application Priority Data

Dec. 17, 2012  (TW) .............................. 101147761 A

(51) Int. Cl.
| | |
|---|---|
| *F21V 7/04* | (2006.01) |
| *F21V 33/00* | (2006.01) |
| *A61L 9/00* | (2006.01) |
| *A61L 2/00* | (2006.01) |
| *F21S 10/04* | (2006.01) |

(52) U.S. Cl.
CPC ............... *F21V 33/0004* (2013.01); *A61L 9/00* (2013.01); *F21S 10/04* (2013.01); *A61L 2/00* (2013.01)

(58) Field of Classification Search
CPC ........................................................ A61L 9/03
USPC .................. 362/555, 96, 109, 217.15, 217.16
See application file for complete search history.

(56) References Cited

U.S. PATENT DOCUMENTS

2007/0091423 A1*  4/2007  Belzunce et al. ............. 359/360

\* cited by examiner

*Primary Examiner* — Vip Patel
(74) *Attorney, Agent, or Firm* — Novak Druce Connolly Bove + Quigg LLP

(57) ABSTRACT

An electronic censer includes a censer body, a driving device and an incense branch. The censer body defines a recess on a top end thereof. The driving device is received in the recess of the censer body. The incense branch is inserted in the censer body and extends from the recess to external environment of the censer body. The incense branch includes a frame and an LED light source located at an upper end of the frame. The LED light source is electrically connected with the driving device. The frame has a first portion and a second portion. The first portion of the frame is pivotally connected with the second portion of the frame, thereby making the second portion of the frame rotatable around the first portion of the frame.

12 Claims, 3 Drawing Sheets

ELECTRONIC CENSER

BACKGROUND

1. Technical Field

The disclosure generally relates to an electronic device, and particularly to an electronic censer with LED (light emitting diode) light source.

2. Description of Related Art

Traditional censers are used for accommodating incenses, each of which mainly includes a rod made of bamboo and aromatic biotic materials coated on the rod. When burned, the aromatic biotic materials release large amounts of smoke. The burning incenses may ignite surrounding articles to fire; furthermore, the released smoke not only pollutes the environment, but also is harmful to health.

Generally, electronic censers are used to replace the traditional censers. An electronic censer includes a censer body and an incense branch extending upwardly from the censer body. The incense branch has an LED (light emitting diode) light source on a top end thereof to imitate a burning tip of the traditional incense. However, the incense branch is relatively long and is therefore easy to break in transportation.

What is needed, therefore, is an electronic censer which can overcome the described limitations.

BRIEF DESCRIPTION OF THE DRAWINGS

Many aspects of the present embodiments can be better understood with reference to the following drawings. The components in the drawings are not necessarily drawn to scale, the emphasis instead being placed upon clearly illustrating the principles of the present embodiments. Moreover, in the drawings, like reference numerals designate corresponding parts throughout the several views.

DETAILED DESCRIPTION

Figure 1:
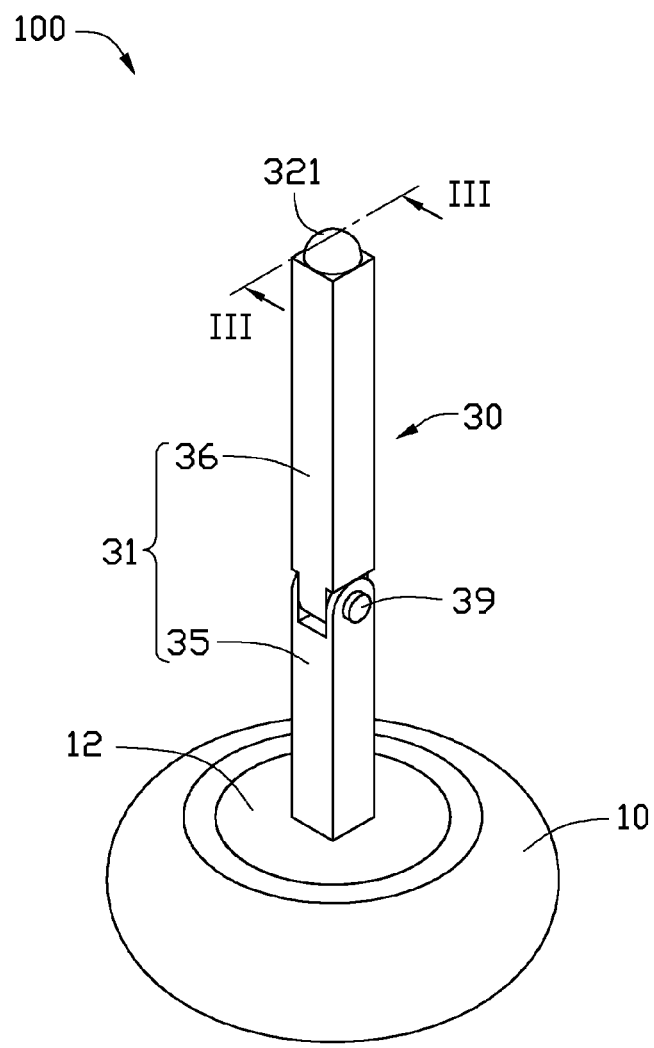
FIG. 1 is an assembled, isometric view of an electronic censer in accordance with one embodiment of the disclosure.
Figure 2:
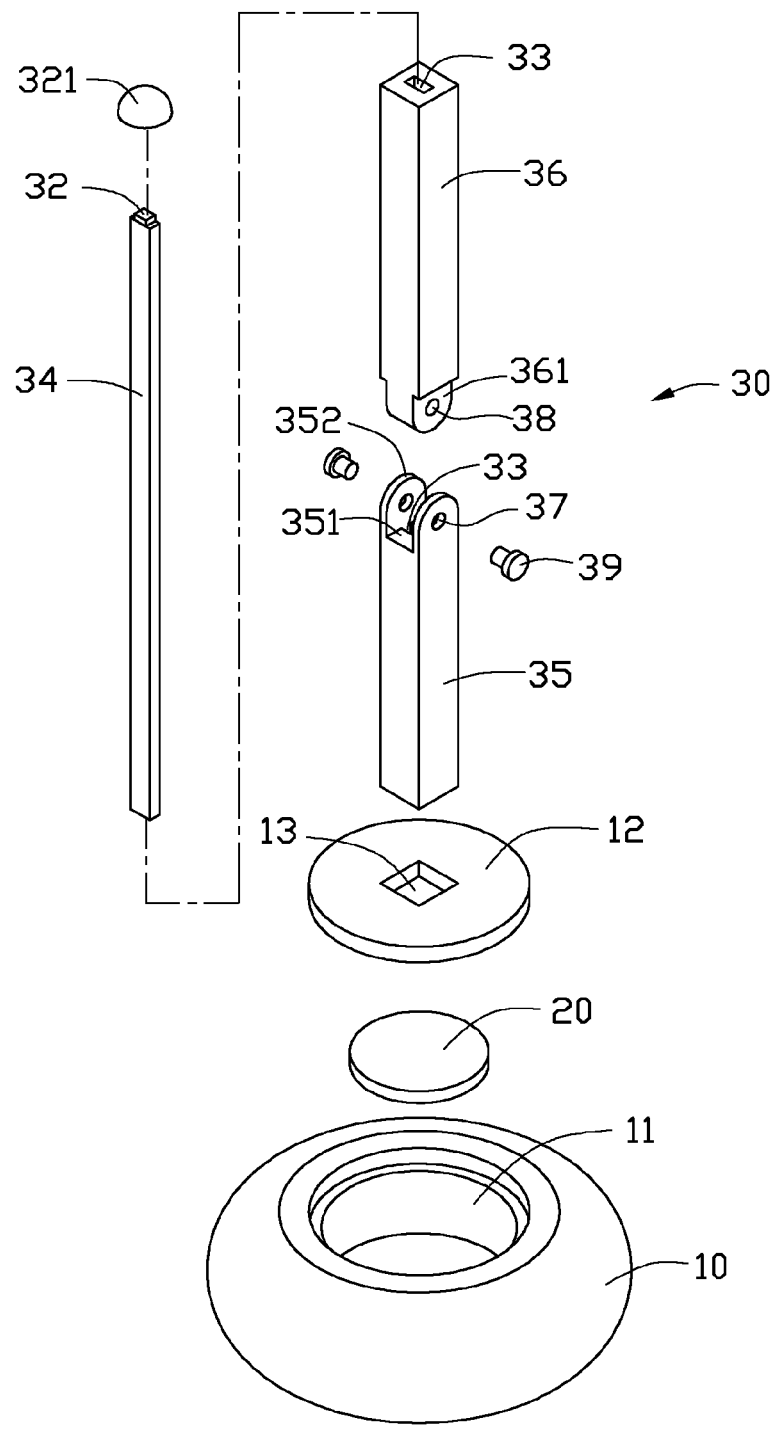
FIG. 2 is an exploded, isometric view of the electronic censer of FIG. 1.
Figure 3:
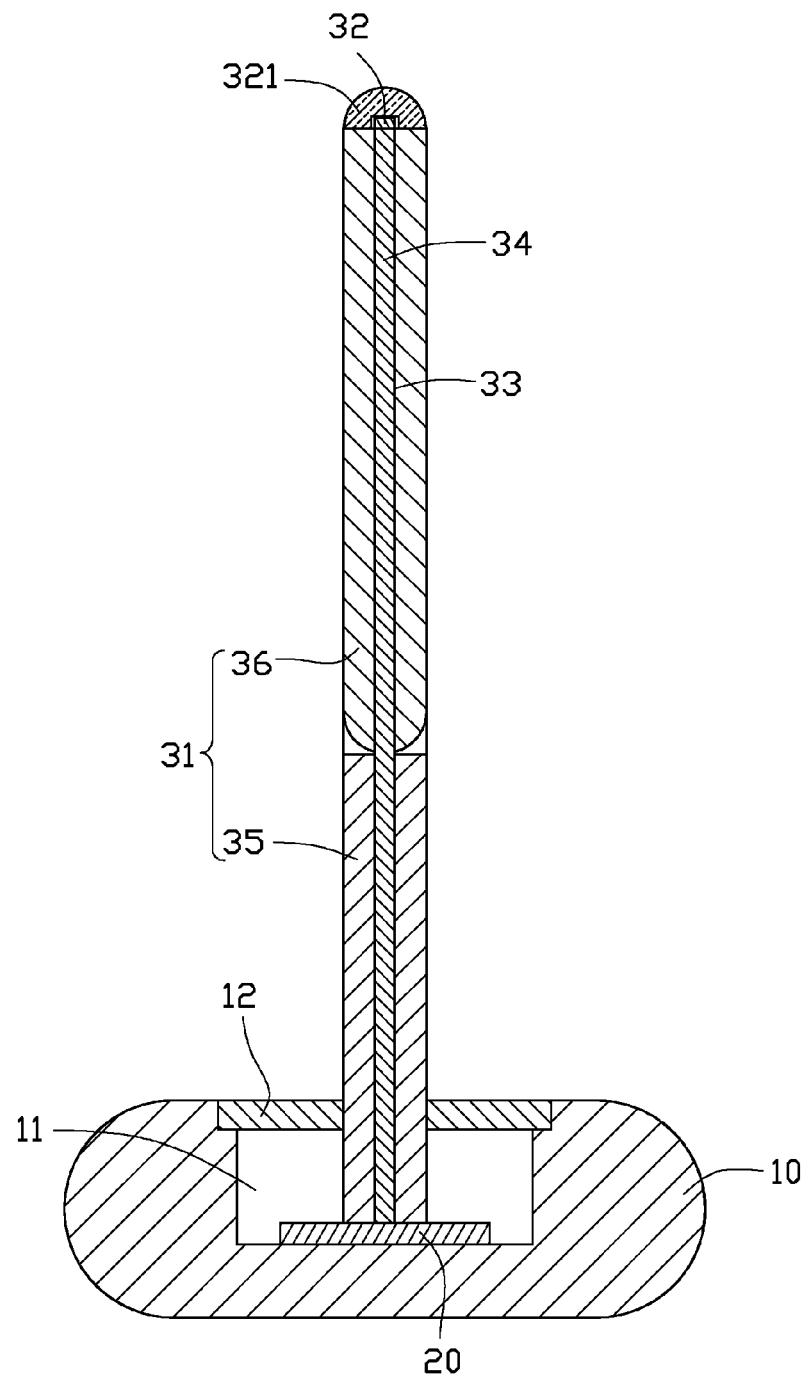
FIG. 3 is a cross sectional view of the electronic censer of FIG. 1, taken along line III-III thereof.

Referring to FIGS. 1-3, an electronic censer 100 in accordance with one embodiment of the disclosure is shown. The electronic censer 100 includes a censer body 10, a driving device 20 and an incense branch 30.

The censer body 10 defines a recess 11 in a top end thereof to receive the driving device 20 and the incense branch 30. In this embodiment, the censer body 10 has a circular shape with a substantially elliptical cross section. Preferably, the censer body 10 can further include a cover 12 located over the recess 11. The cover 12 is removable from the censer body 10. A center portion of the cover 12 defines a through hole 13 for the incense branch 30 to pass through and extend downwardly into the recess 11.

The driving device 20 is received in the recess 11 of the censer body 10. In this embodiment, the driving device 20 is configured to support the incense branch 30 and provide power for the incense branch 30.

The incense branch 30 is inserted inside the censer body 10 and extends from the recess 11 to external environment of the censer body 10. The incense branch 30 includes a frame 31 and an LED light source 32 positioned at a top end of the frame 31. The LED light source 32 is electrically connected with the driving device 20. In this embodiment, the frame 31 is hollow and therefore defines a through hole 33 therein from top to bottom. A flexible printed circuit board 34 is located inside the frame 31 and received in the through hole 33. The flexible printed circuit board 34 has electrical conductive wires (not shown) to electrically connect the LED light source 32 and the driving device 20. The frame 31 has a first portion 35 and a second portion 36. The first portion 35 is pivotally connected with the second portion 36; therefore, the second portion 36 is rotatable relative to the first portion 35. In this embodiment, the first portion 35 of the frame 31 is inserted into the censer body 10. The LED light source 32 is formed on an upper end of the second portion 36 of the frame 31. An upper end of the first portion 35 defines a first opening 37 and a bottom end of the second portion 36 defines a second opening 38. A shaft 39 extends through the first opening 37 and the second opening 38 to make that the first portion 35 is pivotally connected with the second portion 36. Preferably, two tabs 352 extend respectively and upwardly from two opposite sides of the upper end of the first portion 35, and thus define a groove 351 therebetween. The first opening 37 passes through the two tabs 352. A protrusion 361 extends downwardly from the bottom end of the second portion 36. The second opening 36 extends through the protrusion 361. In assembly, the protrusion 361 is inserted in the groove 351, and the shaft 39 extends through the protrusion 361 and the two tabs 352 to make the second portion 36 be rotatable relative to the first portion 35.

Preferably, the incense branch 30 can further include an encapsulation 321. The encapsulation 321 is formed on the upper end of the frame 31 and covers the LED light source 32. The encapsulation 321 is made of a material selected from a group consisting of epoxy resin, silicone, polycarbonate (PC), polymethyl methacrylate (PMMA) and mixtures thereof. In this embodiment, the encapsulation 321 has a semi-elliptical shape. The encapsulation 321 is processed by, for example, sandblasting to form a rough outer surface.

In the electronic censer 100 described above, the frame 31 of the incense branch 30 includes the first portion 35 and the second portion 36 pivotally connected with the first portion 35. In transportation of the electronic censer 100, the second portion 36 is rotated relative to the first portion 35 downwardly. Therefore, the frame 31 is folded, thereby decreasing the length of the incense branch 30. The structure described above makes the incense branch 30 be not easily broken during transportation thereof.

In alternative embodiments, the frame can include three or more portions which are pivotally connected in series to make that the frame is easy to fold for transportation. Furthermore, the electronic censer can further include a voltage transformer. The driving device is electrically connected with external power through the voltage transformer.

It is to be understood, however, that even though numerous characteristics and advantages of the present embodiments have been set forth in the foregoing description, together with details of the structures and functions of the embodiments, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An electronic censer comprising:
   a censer body, defining a recess therein;
   a driving device, received in the recess of the censer body; and
   an incense branch, with one end inserted in the censer body and another end extending out of the censer body, the incense branch comprising a frame and an LED light source located at an upper end of the frame, the LED light source being electrically connected with the driving device, the frame comprising a first portion and a second portion, the first portion of the frame being pivotally connected with the second portion of the frame, thereby making the second portion of the frame rotatable relative to the first portion of the frame.

2. The electronic censer of claim 1, wherein the first portion of the frame is inserted into the censer body, the LED light source is located at an upper end of the second portion of the frame, and an upper end of the first portion of the frame is pivotally connected with a bottom end of the second portion of the frame.

3. The electronic censer of claim 2, wherein the first portion defines a first opening in the upper end thereof, the second portion defines a second opening in the bottom end thereof, and a shaft extends through the first opening and the second opening and makes the second portion pivotally connected with the first portion.

4. The electronic censer of claim 3, wherein the first portion defines a groove in the upper end thereof, the second portion comprises a protrusion on the bottom end thereof wherein the second opening is in the protrusion, the protrusion is inserted into the groove, and the shaft passes through the first opening and the second opening in the protrusion to pivotally connect the first portion with the second portion.

5. The electronic censer of claim 4, wherein two tabs extend respectively from two opposite sides of the upper end of the first portion, and thus define the groove therebetween, and the first opening passes through the two tabs.

6. The electronic censer of claim 1, wherein the frame is hollow and defines a through hole from top to bottom adapted for receiving electrical conductor therein to electrically connect the driving device with the LED light source.

7. The electronic censer of claim 1, wherein the frame is hollow and defines a through hole from top to bottom thereof, the incense branch further comprises a flexible printed circuit board, the flexible printed circuit board is received in the through hole inside the frame, and the flexible printed circuit board electrically connects the driving device with the LED light source.

8. The electronic censer of claim 1, wherein the incense branch further comprises an encapsulation formed on the upper end of the frame and covering the LED light source.

9. The electronic censer of claim 8, wherein the encapsulation is made of a material selected from a group consisting of poxy resin, silicone, polycarbonate, polymethyl methacrylate and mixtures thereof.

10. The electronic censer of claim 8, wherein the encapsulation has a semi-ellipse shape.

11. The electronic censer of claim 8, wherein an outer surface of the encapsulation is processed to form a rough surface.

12. The electronic censer of claim 1, wherein the censer body comprises a cover located on the recess, and the cover defines an opening for the incense branch to pass through and extend into the recess.

* * * * *